US011325959B2

(12) United States Patent
Conduzorgues

(10) Patent No.: US 11,325,959 B2
(45) Date of Patent: May 10, 2022

(54) METHOD FOR MANUFACTURING A STABLE EMULSION FOR PEPTIDE DELIVERY

(71) Applicant: OSE IMMUNOTHERAPEUTICS, Nantes (FR)

(72) Inventor: Jean-Pascal Conduzorgues, Montpellier (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 204 days.

(21) Appl. No.: 16/477,534

(22) PCT Filed: Jan. 24, 2018

(86) PCT No.: PCT/EP2018/051647
§ 371 (c)(1),
(2) Date: Jul. 12, 2019

(87) PCT Pub. No.: WO2018/138110
PCT Pub. Date: Aug. 2, 2018

(65) Prior Publication Data
US 2019/0345213 A1 Nov. 14, 2019

(30) Foreign Application Priority Data

Jan. 25, 2017 (EP) .................................... 17305079

(51) Int. Cl.
| | | |
|---|---|---|
| *C07K 14/00* | (2006.01) | |
| *C07K 14/47* | (2006.01) | |
| *A61K 9/107* | (2006.01) | |
| *A61K 38/10* | (2006.01) | |
| *A61K 38/17* | (2006.01) | |
| *A61K 39/00* | (2006.01) | |

(52) U.S. Cl.
CPC .......... *C07K 14/4748* (2013.01); *A61K 9/107* (2013.01); *A61K 38/10* (2013.01); *A61K 38/17* (2013.01); *A61K 39/0011* (2013.01)

(58) Field of Classification Search
None
See application file for complete search history.

(56) References Cited

FOREIGN PATENT DOCUMENTS

| WO | WO 2004/094454 | 11/2004 |
| WO | WO 2016/070928 | 5/2016 |

OTHER PUBLICATIONS

Smulders, P.E.A., 2000. Formation and stability of emulsions made with proteins and peptides. ISBN: 90-5808-313-6.*
Aucouturier, J. et al. "Montanide ISA 720 and 51: a new generation of water in oil emulsions as adjuvants for human vaccines" *Expert Review of Vaccines*, Jun. 2002, pp. 111-118, vol. 1, No. 1.
Dogru, S. T. et al. "Oral multiple w/o/w emulsion formulation of a peptide salmon calcitonin: in vitro-in vivo evaluation" *Journal of Clinical Pharmacy and Therapeutics*, Dec. 1, 2000, pp. 435-443, vol. 25, No. 6.
Written Opinion in International Application No. PCT/EP2018/051647, dated Jun. 15, 2018, pp. 1-5.

* cited by examiner

*Primary Examiner* — Jeanette M Lieb
(74) *Attorney, Agent, or Firm* — Saliwanchik, Lloyd & Eisenchenk

(57) ABSTRACT

The present invention pertains to a method for manufacturing a ready-to-use peptide emulsion on the industrial scale, comprising the step of emulsifying a suspension of at least two peptides under low shear conditions with at least one adjuvant. It is also directed to a ready-to-use emulsion obtainable according to this method. This invention allows the delivery of a scalable emulsion of peptides which preserves their integrity and fulfills the requirements needed for a pharmaceutical sterile product.

11 Claims, No Drawings
Specification includes a Sequence Listing.

METHOD FOR MANUFACTURING A STABLE EMULSION FOR PEPTIDE DELIVERY

CROSS-REFERENCE TO RELATED APPLICATION

This application is the U.S. national stage application of International Patent Application No. PCT/EP2018/051647, filed Jan. 24, 2018.

The Sequence Listing for this application is labeled "Seq-List.txt" which was created on Jun. 10, 2019 and is 5 KB. The entire content of the sequence listing is incorporated herein by reference in its entirety.

The present invention pertains to a method for manufacturing a ready-to-use peptide emulsion on the industrial scale and to a ready-to-use emulsion obtainable according to this method. This invention allows the delivery of a scalable emulsion of peptides which preserves their integrity and fulfills the requirements needed for a pharmaceutical sterile product.

BACKGROUND OF THE INVENTION

New approaches are being followed for the treatment of cancer, which involve the development of improved cancer vaccines comprising a combination of peptides.

However, the presence of insoluble peptides, the risk of peptide aggregation and the possible resulting decrease in immunogenicity, are recurrent obstacles in the development of protein drugs or peptides drugs. This risk of aggregation or deamidation is increasing between peptides when they are mixed in the same formulation.

Approximately 95% of all peptide drug candidates are discarded during preclinical or clinical trials, often because of problems related to low solubility or aggregation issues. Aggregation is also one of the most significant obstacles to the development of protein-based drugs because it may not only compromise their bioavailability and therapeutic effect but also increase the risk of adverse reactions (*Interpretation of the dissolution of insoluble peptide sequences based on the acid-base properties of the solvent* L Malavolta et al 2006, *Protein Sci.* 2006 June; 15(6): 1476-1488).

Peptides shorter than five residues are usually soluble in water or aqueous buffer, except when the entire sequence consists of hydrophobic amino acids (e.g. A, F, I, L, M, P, V, W, Y, alpha-amino butyric acid, b-amino alanine, norleucine). Peptides containing 50% and more hydrophobic residues might be insoluble or only partly soluble in aqueous solutions. Peptides containing a high proportion (>75%) of D, E, H, K, N, Q, R, S, T, Y are capable of building intermolecular hydrogen bonds (i.e., crosslinking), thus forming gels in aqueous solutions.

Aggregates of peptides are classified as soluble or insoluble, as well as covalent (involving the formation of a covalent bond, often a disulfide linkage) or hydrogen-bonded (weaker interactions). Self-association of therapeutic proteins via covalent bonds is typically irreversible, while aggregates formed via weaker interactions may be reversible upon changes in protein concentration, temperature, and pH. As a result, aggregates can range in size from minute, invisible, non-filterable particles to large precipitates that are visible with the naked eye. In addition, some aggregates may be static while others may be dynamic. Certain manufacturing stages influence the risk of chemical degradation, which increases the risk of physical degradation and the formation of aggregates. For instance, higher concentrations of a protein or peptides formulation can increase the probability of aggregation, as well as changes in solution pH, temperature, buffer choice. Moreover, the emulsification step conducted in the manufacture of vaccines may also cause peptide degradation and aggregation. Vaccine formulations with adjuvants allowing the formation of water-in-oil (W/O) emulsions induce an immune response through the formation of a depot at the injection site and are indeed highly desirable. However, the homogenization and emulsification process is an issue when a combination of peptides includes both soluble and insoluble peptides. The stability of such peptides in the emulsion is critical for safety and immunogenicity as emulsification is a key element for local delivery of peptides and immune presentation. The peptides in soluble or insoluble states are both sensitive to temperature and agitation, they are sensitive to oxidation, the mixture of insoluble and soluble peptides can present cross-reactivity concerns during storage, and the mechanical forces used to mix such combination can alter the peptides.

In view of these shortcomings, vaccine formulations comprising peptide combinations are rather prepared extemporaneously.

For instance, a recent study was conducted with combined peptides URLC19-177, CDCA1-56, TTK-567, VEGFR1-770 and VEGFR2-169; all five peptides were expected to bind to an HLA-A24 molecule. Peptides combined were all dissolved in DMSO at the concentration of 20 mg/ml and stored at −80° C. They were injected at bed place after mixing with an adjuvant (incomplete Freunds adjuvant IFA or Montanide® ISA 51) (Suzuki H. et al 2013 *"Multiple therapeutic peptide vaccines consisting of combined novel cancer testis antigens and anti-angiogenic peptides for patients with non-small cell lung cancer." Journal of Translational Medicine* 2013). Similar combined peptides were used with the same process (TTK-567, URLC10-177, KOC1-508, VEGFR1-1084, VEGFR2-169 bounding to the HLA-A*24 molecule (Iinuma H. et al *"Phase I clinical study of multiple epitope peptide vaccine combined with chemoradiation therapy in esophageal cancer patients"—Journal of Translational Medicine* 2014). Five HLA-A*2402-restricted peptides derived from RNF43, TOMM34, KOC1, VEGFR1, and VEGFR2 were also used in combination [RNF43-721, TOMM34-299, KOC1(IMP-3)-508, VEGFR1-1084 and VEGFR2-1691 (Hazama S. et al *"A phase I study of combination vaccine treatment of five therapeutic epitope-peptides for metastatic colorectal cancer; safety, immunological response, and clinical outcome" Journal of Translational Medicine* 2014).

All the peptide combinations presented above in the recent literature are first solubilized and then mixed with an adjuvant just before injection to the patients. This process avoided the preparation of an emulsion in which long-term stability of the peptides in the adjuvant would have been required.

On the contrary, an example of a ready-to-use vaccine comprising a mixture of peptides is disclosed in WO 2004/094454. In this document, the combination of peptides is administered subcutaneously in the form of a reverse emulsion. In order to prepare said emulsion, the various soluble and insoluble peptides are solubilized in different media, to provide three separate solutions which are then cooled, subjected to sterile filtration and blended together so as to obtain a suspension, the pH of which is then adjusted to 7. This suspension is mixed with a water-in-oil (W/O) emulsifier comprising mannide mono-oleate obtained from mannitol and purified oleic acid of synthetic or vegetable origin. This emulsifier allows obtaining a water-in-oil emulsion containing fine droplets of water in which the peptides are dispersed. This emulsion structure in turn provides for a strong and long lasting immunity.

Emulsification of peptides requires a powerful mixer. Homogenization uses mechanical forces to mix the oil coming from the adjuvant and the water droplets coming from the peptide solutions. High shear and mechanical forces are important to create finely dispersed droplets. This emulsion oftentimes proves troublesome, given that peptide chemistries impart resistance on the mixing process. The high shear achieved by a high pressure homogenizer is able to overcome that resistance. Suppliers of adjuvants thus recommend the emulsification of peptides with high shear. For example, in the brochure dated April 2007 describing the adjuvant sold as Montanide® ISA 50 V2, SEPPIC suggests mixing this adjuvant with an aqueous antigenic medium using a high shear mixer such as Silverson® L4RT at 4000 rpm for obtaining a stable and efficient vaccine.

In line with the above, in WO 2004/094454, mixing of the peptide suspension with the adjuvant was performed using a Silverson® L4RT homogenizer rotating at 8,000 rpm for 30 minutes. This apparatus comprises a mixing workhead having a rotor provided with blades that are radially arranged around an axis and which direct the fluid drawn by the rotor radially to a stator disposed concentrically from and at a short distance of the rotor. The stator comprises holes provided in a grid. Such a rotor-stator system provides the emulsion formed in WO 2004/094454 with a high shear since it is milled between the ends of the rotor blades and the inner wall of the stator and forced at high velocity out through the perforations in the stator, towards the sides of the mixing workhead.

However, the present inventors have shown that the scale-up of this process did not result in an emulsion providing for long-term stability of the peptides. Specifically, when scaling up the above process, it came to the Applicant's attention that the dosage of peptides contained therein by reverse-phase HPLC led to different values depending on the batches that were tested. This was already noted in WO 2004/094454 where it is stated that errors up to 30% in peptide concentration were observed. This variability was acceptable for a final pharmaceutical product, as the specification of 50% of the intended concentration was proposed as a release and stability criterion. Although this variability remained within an acceptable range for early clinical studies, it would be necessary for the purpose of advanced clinical trials to reduce it as much as possible, in order to comply with the strict requirements of some pharmaceutical legislation and more importantly to ensure the delivery of peptides in a stable emulsified state and to guarantee the immunogenicity of each peptide. The Inventors have conducted extensive research to overcome this problem.

In this context, it has been shown by the present inventors that the speed and the duration of agitation that are required to obtain a valuable emulsification of peptides with adjuvant in cancer vaccines can alter peptide integrity and reduce their efficacy, in particular when the combination is made by soluble and insoluble peptides.

It was found that the emulsification method with high shear and high speed led to peptide degradation and/or aggregation when used on a large scale. Moreover, the high shear mixer used in the prior art generated heat and thus required constant cooling of the mixer so as to avoid a possible degradation of heat-sensitive peptides. When scaling up this process, the accurate control of this cooling step appeared to be a challenge in order to avoid peptide oxidation, which could detrimentally affect their efficacy depending on the position of oxidized amino acids relative to the functional or epitope-like domains of the peptide. Oxidation can also alter the physicochemical characteristics of peptides and lead to aggregation. This phenomenon could in turn compromise the safety and delivery necessary for the therapeutic effect of drugs containing these peptides and also increase the risk of immunogenic reactions.

The inventors thus searched for means to overcome the above problems and thus provide a process which may be easily performed on the industrial scale to prepare an injectable peptide emulsion in which the chemical integrity of peptides is preserved, in particular peptide degradation (such as oxidation and/or deamidation) and aggregation is prevented or reduced, without negatively impacting the physical stability of the emulsion, such that each peptide is delivered in stable conditions. In addition, a reproducible process is needed.

SUMMARY

The Applicant has surprisingly found that the above requirements could be met by a process in which the peptide emulsion is prepared under milder conditions than the emulsification conditions used so far. Specifically, contrary to what was recommended in the art, high speed and high shear are avoided and, more surprisingly, even at low speed a long duration of mixing is not necessary. Peptides of different solubilities are thus protected from oxidative stress without the need for cooling the emulsion while mixing, and their aggregation is prevented. The variability of peptide concentration is thus dramatically reduced compared to the prior art such as WO 2004/094454. This invention thus allows obtaining a stable emulsion for optimal delivery of peptides which is required for stable immunogenicity due to the depot effect necessary for peptide immune presentation. This process is further more reproducible than former processes for the extemporaneous preparation of peptides emulsions, since the latter are operator-dependent. It allows the manufacture of a large volume of emulsion and is thus applicable on an industrial scale.

This invention is thus directed to a method for manufacturing a ready-to-use peptide emulsion on the industrial scale, comprising the step of emulsifying a suspension of at least two peptides under low shear conditions, at a rotation speed of between 100 and 1000 rpm, during 2 to 15 minutes, with at least one adjuvant.

Preferably, the peptides comprise at least one soluble peptide and at least one non-soluble peptide. In particular, the peptides are selected from the group consisting of: a peptide KVFGSLAFV (SEQ ID NO:7), a peptide YLSGADLNL (SEQ ID NO:8), a peptide KLBPVQLWV with B indicating α-aminoisobutyric acid (SEQ ID NO:6), a peptide SMPPPGTRV (SEQ ID NO:5), a peptide IMIGHLVGV (SEQ ID NO:9), a peptide LLTFWNPPV (SEQ ID NO:4), a peptide RLLQETELV (SEQ ID NO:2), a peptide aKXVAAWTLKAAa with X and a respectively indicating cyclohexylalanine and d-alanine (SEQ ID NO:1), a peptide YLQLVFGIEV (SEQ ID NO:3) and a peptide KVAEIVHFL (SEQ ID NO:10). In a specific embodiment, the suspension comprises a combination of a peptide KVFGSLAFV (SEQ ID NO:7), a peptide YLSGADLNL (SEQ ID NO:8), a peptide KLBPVQLWV (SEQ ID NO:6), a peptide SMPPPGTRV (SEQ ID NO:5), a peptide IMIGHLVGV (SEQ ID NO:9), a peptide LLTFWNPPV (SEQ ID NO:4), a peptide RLLQETELV (SEQ ID NO:2), a peptide aKXVAAWTLKAAa with X and a respectively indicating cyclohexylalanine and d-alanine (SEQ ID NO:1), a peptide YLQLVFGIEV (SEQ ID NO:3) and a peptide KVAEIVHFL (SEQ ID NO:10).

Preferably, the adjuvant consists of a mixture of a hydrocarbon oil with a water-in-oil emulsifier. In particular, the hydrocarbon oil is selected from paraffin oil, a vegetable oil, squalene, squalane or a mineral oil and the water-in-oil emulsifier is selected from mannide mono-oleate and sorbitan mono-oleate. In a specific embodiment, the hydrocarbon oil is a mineral oil and the water-in-oil emulsifier is selected from mannide mono-oleate.

Preferably, the weight ratio of the adjuvant to the peptide suspension ranges from 10:1 to 1:10, preferably from 5:1 to 1:5 and more preferably from 2:1 to 1:2 and still preferably is of 1:1.

Preferably, all or part of the mixing step is performed under inert atmosphere, preferably under nitrogen.

Preferably, the volume of the emulsion is greater than 5 L, preferably greater or equal to 10 L. In a particular embodiment, the peptide suspension is prepared by a method comprising:

a) preparing at least three different solutions A, B and C, wherein:
  solution A being an acidic aqueous medium and comprising a peptide aKXVAAWTLKAAa (SEQ ID NO:1) with X and a respectively indicating cyclohexylalanine and d-alanine (SEQ ID NO:1),
  solution B being a basic aqueous medium with a pH of between 12.5 and 12.9 before adding any peptide thereto and solution B comprising a peptide YLSGADLNL (SEQ ID NO:8),
  solution C being DMSO and comprising a peptide KVFGSLAFV (SEQ ID NO:7), and
  solutions A and/or B further comprise at least three additional peptides selected from: KLBPVQLWV with B indicating α-aminoisobutyric acid (SEQ ID NO:6), SMPPPGTRV (SEQ ID NO:5), IMIGHLVGV (SEQ ID NO:9), LLTFWNPPV (SEQ ID NO:4), KVAEIVHFL (SEQ ID NO:10), RLLQETELV (SEQ ID NO:2) and YLQLVFGIEV (SEQ ID NO:3);

b) mixing said solutions so as to form a suspension, and
c) adjusting the pH of said suspension to about 7.

In one aspect, the solution A comprises aKXVAAWTLKAAa (SEQ ID NO:1), SMPPPGTRV (SEQ ID NO:5), IMIGHLVGV (SEQ ID NO:9) and KVAEIVHFL (SEQ ID NO:10) and the solution B comprises YLSGADLNL (SEQ ID NO:8), KLBPVQLWV (SEQ ID NO:6), LLTFWNPPV (SEQ ID NO:4), RLLQETELV (SEQ ID NO:2) and YLQLVFGIEV (SEQ ID NO:3).

The present invention also relates to a ready-to-use emulsion obtainable or obtained by the method according to the present invention, especially for use in the treatment of cancers, preferably of HLA-2 positive cancers. In particular, the amount of each peptide in the emulsion ranges from 0.1 to 10 mg/ml, preferably from 0.5 to 1 mg/ml and does not differ by more than 10% from the amount that was used in the preparation of the emulsion. In one embodiment, the D50 of the emulsion is 10±1 μm.

DETAILED DESCRIPTION

This invention pertains to a method for manufacturing, on an industrial scale, a ready-to-use emulsion from a peptide suspension comprising at least two peptides. These peptides usually do not have the same solubility and it is preferred to use a combination of at least one soluble and at least one non-soluble peptides.

The expression "non-soluble peptide" refers to a peptide which is soluble in an amount of less than 60% w/v in water at a pH of 7.0±1.0, whereas a "soluble peptide" refers to a peptide which is soluble in an amount of at least 60% w/v in water at a pH of 7.0±1.0. Solubility may be assessed by passing an aqueous solution of the peptide, at a concentration of 1 mg/ml, through a 0.45 μm filter and measuring the amount of peptide remaining on the filter.

By "industrial scale", it is meant that a volume greater than 5 L, preferably greater or equal to 10 L, of the emulsion is prepared. In one embodiment, the volume can be 50 L, 100 L, 200 L, 500 L or 1000 L.

Peptides

According to a preferred embodiment of this invention, the peptides may be selected from Tumor-associated antigen (TAA) epitopes and/or analogs thereof, preferably HLA-A2 binding TAA epitopes.

TAA epitopes can be derived from one or several targets, in particular selected from the group consisting of CEA (Carcinoembryonic antigen), p53, HER-2/neu, MAGE (Melanoma antigen), in particular MAGE-2 and MAGE-3, LY6K (Lymphocyte Antigen 6 Complex, Locus K), CDCA1 (cell division cycle associated 1) (for instance see EP2186889), IMP3 (insulin-like growth factor-II mRNA-binding protein 3) (for instance see WO11067920), KIF20A (Kinesin-like protein) (for instance see WO10047062), FOXM1 (Forkhead box protein M1) (for instance see EP2186889), CDC45L (Cell division control protein 45 homolog), GPC3 (glypican-3) (for instance see WO2015/173112), CDH3 (Cadherin 3), SPARC (Secreted Protein Acidic And Cysteine Rich), DEPDC1 (DEP domain containing 1), MPHOSPH1 (M-PHASE PHOSPHOPROTEIN 1) (for instance see WO2013024582), ME-1 (Malic Enzyme 1), ENDC3B, PRDX5 (Peroxiredoxin-5), GAS7 (Growth arrest-specific protein 7), HA-1 (miHAg) (Minor histocompatibility antigen HA-1), GAPDH (Glyceraldehyde 3-phosphate dehydrogenase), HSP70 (70 kD heat shock proteins), ACTININ, HAUS3 (HAUS augmin-like complex subunit 3), CSNK1A1 (Casein kinase I isoform alpha), CLPP (ATP-dependent Clp protease proteolytic subunit) and CDK4 (Cyclin-dependent kinase 4). In a preferred embodiment, the peptides are selected and target CEA, p53, HER-2/neu, MAGE-2 and MAGE-3.

For instance, the peptides includes peptides selected from the peptides disclosed in WO 2004/094454, WO2014141683, WO2015173112, WO2015160928, WO2015/155537, WO2014162962, WO2014141652, WO2014136453, WO2014136453, WO2014127276, WO2014047085, WO2014041784, WO2013024582, WO2012073459, WO2013061594, WO2012169200, WO2011111392, WO2012053200, WO2012053206, WO2010137295, WO08047473, WO08102557, WO09109855, EP2186889, EP2186889, WO2010047062, WO2011067920 and the like (the disclosure thereof being incorporated herein by reference). According to a specific embodiment of this invention, the peptides are selected from the group consisting of: a peptide KVFGSLAFV (SEQ ID NO:7), a peptide YLSGADLNL (SEQ ID NO:8), a peptide KLBPVQLWV with B indicating α-aminoisobutyric acid (SEQ ID NO:6), a peptide SMPPPGTRV (SEQ ID NO:5), a peptide IMIGHLVGV (SEQ ID NO:9), a peptide LLTFWNPPV (SEQ ID NO:4), a peptide RLLQETELV (SEQ ID NO:2), a peptide aKXVAAWTLKAAa with X and a respectively indicating cyclohexylalanine and d-alanine (SEQ ID NO:1), a peptide YLQLVFGIEV (SEQ ID NO:3), a peptide KVAEIVHFL (SEQ ID NO:10). At least two of these peptides can be used in this invention, preferably at least three, such as aKXVAAWTLKAAa (SEQ ID NO:1), YLSGADLNL (SEQ ID NO:8) and KVFGSLAFV (SEQ ID NO:7), and still preferably a combination of all the above ten peptides. In a particular embodiment, the peptides further comprise one or several additional peptides.

In a particular embodiment, the peptides may comprise a peptide selected from the group consisting of FLDEFMEGV (SEQ ID NO:11), VVMSWAPPV (SEQ ID NO:12), LLL-DDLLVSI (SEQ ID NO:13), SLADEAEVYL (SEQ ID NO:14), VLHDDLLEA (SEQ ID NO:15), GIVEGLITTV (SEQ ID NO:16), SLFEGIDIYT (SEQ ID NO:17), FIASNGVKLV (SEQ ID NO:18), ILNAMIAKI (SEQ ID NO:19), GLFGDIYLAI (SEQ ID NO:20), ILDKVLVHL (SEQ ID NO:21), and ACDPHSGHFV (SEQ ID NO:22).

The nomenclature used to describe peptides in this application follows the conventional practice wherein the amino group is presented to the left (the amino- or N-terminus) and the carboxyl group to the right (the carboxy- or C-terminus) of each amino acid residue. The amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acid residues having D-forms is represented by a lower case single letter or a lower case three letter symbol. For instance, the symbol "a" refers to a D-alanine. The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine). In addition to these symbols, "B" in the single letter abbreviations used herein designates a-amino butyric acid and "X" indicates cyclohexylalanine.

Suspension

The peptide suspension used in this invention may be prepared according to a process comprising preparing at least two different solutions containing the at least two different peptides, respectively. According to an embodiment of this invention, three different solutions A, B and C are prepared, which each contain at least one specific peptide. In particular, solution A is an acidic aqueous medium, solution B is a basic aqueous medium and solution C is an organic medium, especially DMSO (dimethylsulfoxide). In a preferred embodiment, solutions A, B and C comprise at least aKXVAAWTLKAAa (SEQ ID NO:1), YLSGADLNL (SEQ ID NO:8) and KVFGSLAFV (SEQ ID NO:7), respectively.

Still preferably, solutions A and/or B further comprise at least three additional peptides, preferably at least five additional peptides, among the above list of peptides. More preferably, solutions A and/or B comprise all these seven additional peptides. Each of these additional peptides will be comprised within Solution A or Solution B depending on its solubility and on its affinity with aKXVAAWTLKAAa (SEQ ID NO:1) or YLSGADLNL (SEQ ID NO:8).

Accordingly, in one aspect, the present invention relates to a method for manufacturing a peptide suspension, comprising:

a) preparing at least three different solutions A, B and C, wherein:
solution A comprises a peptide aKXVAAWTLKAAa with X and a respectively indicating cyclohexylalanine and d-alanine (SEQ ID NO:1),
solution B comprises a peptide YLSGADLNL (SEQ ID NO:8),
solution C comprises a peptide KVFGSLAFV (SEQ ID NO:7), and
solutions A and/or B further comprise at least three additional peptides selected from: KLBPVQLWV with B indicating α-aminoisobutyric acid (SEQ ID NO:6), SMPPPGTRV (SEQ ID NO:5), IMIGHLVGV (SEQ ID NO:9), LLTFWNPPV (SEQ ID NO:4), KVAEIVHFL (SEQ ID NO:10), RLLQETELV (SEQ ID NO:2) and YLQLVFGIEV (SEQ ID NO:3);

b) mixing said solutions so as to form a suspension, and c) adjusting the pH of said suspension to about 7, and preferably the pH of solution B is adjusted between 12.5 and 12.9 before adding any peptide thereto.

Solution A is preferably prepared by solubilizing the peptides in an acidic aqueous medium, such as an acetic acid solution, preferably at room temperature. The concentration of the acetic acid solution may range from 0.1 M to 0.3 M, for instance. Accordingly, the acidic aqueous medium has a pH which is preferably comprised between 2 and 4, more preferably between 2.5 and 3. Each peptide of solution A can be present at a concentration of 0.3 mg/ml to 4 mg/ml, preferably 3 to 4 mg/ml. Preferably, all the peptides are present in solution A at the same concentration. Preferably, solution A comprises aKXVAAWTLKAAa (SEQ ID NO:1), and one, two or three peptides selected from the group consisting of SMPPPGTRV (SEQ ID NO:5), IMIGHLVGV (SEQ ID NO:9) and KVAEIVHFL (SEQ ID NO:10). In a most preferred embodiment, solution A comprises aKXVAAWTLKAAa (SEQ ID NO:1), SMPPPGTRV (SEQ ID NO:5), IMIGHLVGV (SEQ ID NO:9) and KVAEIVHFL (SEQ ID NO:10). In a particular embodiment, the peptides of solution A consist in aKXVAAWTLKAAa (SEQ ID NO:1), SMPPPGTRV (SEQ ID NO:5), IMIGHLVGV (SEQ ID NO:9) and KVAEIVHFL (SEQ ID NO:10).

Moreover, solution B may be prepared by solubilizing the peptides in a basic aqueous medium, for instance a sodium hydroxide solution, usually at room temperature.

When scaling up the above process, it came to the Applicant's attention that one of the peptides contained in the basic solution (namely YLSGADLNL (SEQ ID NO:8)) was not chemically stable for long enough to allow sterile filtration of this solution on the industrial scale.

The Applicant has surprisingly found that a slight adjustment in the pH of the basic solution to which the YLSGADLNL (SEQ ID NO:8) peptide should be added allowed avoiding its degradation. Therefore, the method of the present invention is suitable for preparing a suspension with a long stability and a good reproducibility.

Indeed, the pH of solution B is adjusted between 12.5 and 12.9 before adding any peptide thereto, preferably about 12.7. It may be obtained by using a 0.05 M solution of sodium hydroxide. Preferably, each peptide in solution B is in a total amount from 0.4 to 3 mg/ml. More preferably, each peptide in solution B can be present at a concentration of 2 mg/ml to 3 mg/ml. Preferably, all the peptides are present in solution B at the same concentration. Preferably, solution B comprises YLSGADLNL (SEQ ID NO:8), and one, two, three or four peptides selected from the group consisting of KLBPVQLWV (SEQ ID NO:6), LLTFWNPPV (SEQ ID NO:4), RLLQETELV (SEQ ID NO:2) and YLQLVFGIEV (SEQ ID NO:3). In a most preferred embodiment, solution B comprises YLSGADLNL (SEQ ID NO:8), KLBPVQLWV (SEQ ID NO:6), LLTFWNPPV (SEQ ID NO:4), RLLQETELV (SEQ ID NO:2) and YLQLVFGIEV (SEQ ID NO:3). In a particular embodiment, the peptides of solution B consist of YLSGADLNL (SEQ ID NO:8), KLBPVQLWV (SEQ ID NO:6), LLTFWNPPV (SEQ ID NO:4), RLLQETELV (SEQ ID NO:2) and YLQLVFGIEV (SEQ ID NO:3).

Finally, solution C may be prepared by solubilizing the KVFGSLAFV peptide (SEQ ID NO:7) in DMSO, preferably in an amount of from 1 to 11 mg/ml, more preferably in an amount of from 10 to 11 mg/ml, at a temperature which is preferably between 35 and 40° C. Preferably, the peptide in solution C can be present at a concentration of 5 mg/ml to 11 mg/ml. In a particular embodiment, the peptides in solution C consist in KVFGSLAFV (SEQ ID NO:7).

According to a preferred embodiment of this invention, solution A comprises aKXVAAWTLKAAa (SEQ ID NO:1), SMPPPGTRV (SEQ ID NO:5), IMIGHLVGV (SEQ ID NO:9) and KVAEIVHFL (SEQ ID NO:10) and solution B comprises YLSGADLNL (SEQ ID NO:8), KLBPVQLWV (SEQ ID NO:6), LLTFWNPPV (SEQ ID NO:4), RLLQETELV (SEQ ID NO:2) and YLQLVFGIEV (SEQ ID NO:3).

All the above peptides are epitopes derived from CEA, p53, HER-2/neu and MAGE-2/3, except PADRE which is a universal pan-DR HTL epitope used as a source of T-cell help.

However, solution A, B or C may further comprise additional tumor-associated antigenic peptides.

As mentioned above, solutions A, B and C are combined in order to obtain a suspension. In a preferred embodiment, solutions A, B and C are combined in a ratio allowing to obtain the same concentration in the suspension for each peptide. Preferably, the solutions A, B and C are combined in order to obtain a suspension in a A:B:C mass ratio of 2-4:3-4:1, more preferably in a mass ratio of 2.9:3.6:1. Preferably, the concentration of each peptide in the suspension is comprised between 0.2 and 2 mg/ml.

According to a preferred embodiment, the solutions are cooled down to a temperature between 2 and 8° C. and subjected to sterile filtration before forming the suspension.

Preferably, solution B is combined with solutions A and C less than 8 hours after its preparation, preferably less than 6 hours and more preferably no more than 4 hours.

The pH of the suspension thus obtained may be adjusted to physiological pH, thus to a pH of about 7, by any suitable means. The peptide concentration may further be adjusted by adding a suitable diluent to the suspension, such as water, a saline solution, an aqueous dextrose solution or a glycerol solution.

In a particular embodiment, there is no filtration step after the step of mixing solutions A, B and C and/or after the step of adjusting the pH to about 7.

In a preferred embodiment, the steps of the method for manufacturing a peptide suspension are carried out under saturated nitrogen conditions so as to avoid any risk of oxidation which could damage the peptides, especially the soluble peptide(s), of the suspension.

The present invention also relates to a sterile container comprising a suspension prepared by the method according to the present invention. Preferably, the sterile container is a glass vial.

Ready to Use Emulsion

This invention then consists in mixing the peptide suspension with an adjuvant so as to obtain a water-in-oil emulsion, which is deemed to help presentation of the peptides to the dendritic cells. In this kind of emulsion, the water phase containing the peptides is entrapped in the form of droplets in the oil continuous phase, which allows for slower release of antigens from a depot and therefore stronger long-term immunity as compared to oil-in-water emulsions.

By "adjuvant", it is meant in the present specification a compound or a mixture of compounds which is/are able to increase the immune response generated by the peptides and direct this immune response, for instance towards a CTL (Cytotoxic T lymphocyte) response. They may act either directly on the immune system, or indirectly, by enabling the suitable delivery of the peptides to the immune system. In this invention, the adjuvant is preferably an oily adjuvant, which comprises both a hydrocarbon oil and a water-in-oil emulsifier. Such adjuvants act by the so-called "deposition effect". The hydrocarbon oil may be paraffin oil, a vegetable oil, squalene, squalane or mineral oil, for instance. Suitable W/O emulsifiers may be selected from mannide mono-oleate and sorbitan mono-oleate, for instance. Examples of appropriate oily adjuvants are a mixture of 5-20% mannide mono-oleate with 80-95% mineral oil (Montanide® ISA 51 sold by SEPPIC) or squalene (Montanide® ISA 720 sold by SEPPIC) and similar mixtures. In a specific embodiment, the adjuvant is a mixture of mineral oil and mannide mono-oleate, especially Montanide® ISA 51.

The adjuvant used in this invention may alternatively, or in addition to the above oily adjuvants, be selected from micro- and nanoparticles, such as liposomes and microspheres, of PLG, PLA, PLGA or other natural polymers such as gelatin, collagen and chitosan. Other adjuvants may comprise TLR ligands, Toll-like receptor ligands (TLR3 and TLR9), stimulators of IFN genes (STING) agonists, cytokines such as GM-CSF and IL2, carbohydrates, bacterial derivatives, mineral salts and immune stimulating complexes (ISCOM).

The suspension and the adjuvant are mixed, according to this invention, under low shear conditions, by means of a mixing device rotating at a rotation speed of 100 to 1000 rpm. For instance, the rotation speed may be comprised within the range of from 100 to 500 rpm, preferably from 150 to 250 rpm, especially it may be 200 rpm. By "low shear", it is meant that mixing is not performed by means of a rotor-stator device, such as (but not limited to) those sold by SILVERSON under the trade name Silverson® L4RT or Silverson® L5M or by IKA WERKE under the trade name Ultra-Turrax®. Then, the emulsifying step is carried out under low shear conditions, in particular at a rotation speed of 100 to 1000 rpm, preferably during 2 to 20 minutes. In one embodiment, the emulsifying step is carried out under low shear conditions at a rotation speed of 100 to 1000 rpm during 2 to 20 minutes. Preferably, the mixing or emulsifying step is conducted, in this invention, by means of a paddle-type mixer or axial flow turbine. For instance, the mixer can be a paddle-type mixer and have a 4-pitch blade impeller, in particular a horizontal 4-pitch blade impeller. This kind of device comprises a mixing head which is an axial flow impeller, not a radial flow rotor as can be found in rotor-stator devices. Therefore, in one embodiment, the mixer is an axial flow impeller. In another embodiment, the mixer is a radial flow impeller. Moreover, it is not encased in a perforated stator.

In one preferred embodiment, the method for manufacturing the ready-to-use peptide emulsion does not comprise any emulsifying step with high shear. In particular, it does not comprise any emulsifying step at a speed higher than 7000, 6000 or 5000 rpm, preferably any mixing step at a speed higher than 2000 rpm. Preferably, the method does not comprise any emulsifying step carried out with a high shear mixer (Silverson® Verso) having a rotor-stator configuration.

In one preferred embodiment, the method for manufacturing the ready-to-use peptide emulsion does not comprise any mixing step with high shear. In particular, it does not comprise any mixing step at a speed higher than 7000, 6000 or 5000 rpm, preferably any mixing step at a speed higher than 2000 rpm. Preferably, the method does not comprise any mixing step carried out with a high shear mixer (Silverson® Verso) having a rotor-stator configuration.

Preferably, to obtain the emulsion, the adjuvant is mixed with the peptide suspension, under aseptic conditions. The adjuvant:suspension weight ratio may be comprised in the range of from 10:1 to 1:10, preferably from 5:1 to 1:5 and more preferably from 2:1 to 1:2 and still preferably is of 1:1.

This mixing or emulsifying step is preferably performed at a temperature of 10 to 30° C., preferably from 20 to 25° C., for 2 to 30 min, for instance from 5 to 15 minutes. It should be noted that the duration of mixing is calculated from the moment where all the adjuvant has been added to the mixing chamber, wherein this addition may be performed in stages. For instance, the adjuvant is added to the suspension during 30 seconds to 3 minutes, preferably during 1 to 2 minutes, at a rotation speed in the range of from 100 to 1000 rpm and preferably from 100 to 500 rpm, more preferably from 100 to 200 rpm. Then, the method may comprise a step of adding the adjuvant to the suspension in the mixing chamber, during a period of 30 seconds to 3 minutes at a temperature of from 10 to 30° C. with an agitation speed in the range of from 10 to 1000 rpm, a step of mixing at 10-30° C. during 2 to 20 minutes at a speed of from 100 to 1000 rpm and optionally a step of recovering the peptide emulsion, wherein the volume of the peptide emulsion is greater than 5 L. All or part of the above mixing step is preferably performed under inert atmosphere, preferably under nitrogen.

A ready-to-use peptide emulsion having a volume greater than 5 L, preferably greater or equal to 10 L, may thus be obtained. It may be used to prepare about 8000 vials for injection.

The peptide emulsion obtained according to this invention is physically stable. Physical stability of the emulsion may be assessed by measuring the water droplet size after 3 month storage at −20, 5 and 25° C., which should not substantially differ from their size immediately after manufacturing the emulsion. The droplet size may be measured by laser diffraction. According to a preferred embodiment, the D50 of the emulsion is 10±2 µm. Moreover, the emulsion should not separate between two layers under the same storage conditions.

Moreover, the peptides are both chemically stable and also biologically stable. By "chemically stable", it is intended to mean, inter alia, that the peptides do not substantially degrade, in particular by oxidation and/or deamidation, and do not substantially aggregate together. The chemical stability of peptides may be measured by liquid phase chromatography coupled with mass spectrometry, after three month storage at room temperature, as shown in the Examples below. Preferably, the amount of each peptide in the emulsion ranges from 0.1 to 10 mg/ml, preferably from 0.5 to 1 mg/ml and does not differ by more than 10% from the amount that was used in the preparation of the emulsion. Their biological stability may be assessed by measuring the immunogenicity of the peptides, for instance by a transgenic in vivo potency test.

The ready-to-use formulation of this invention thus complies with industry regulations for consistent manufacture and quality control of a vaccine product.

The emulsion may be stored at a temperature of 2 to 8° C. or even frozen after manufacturing and brought to room temperature before use. This emulsion may be conditioned in a vessel having a volume of from 1 to 50 ml.

One of the advantages of the ready-to-use emulsion of the invention is that this emulsion can be frozen and de-frozen, in particular without any or with limited impact on the structure of the emulsion. Therefore, the present invention relates to a ready-to-use emulsion according to the present invention suitable for freezing and de-freezing, i.e. while maintaining or preserving the emulsion.

It may be administered parenterally as a ready-to-use vaccine to elicit T-lymphocyte responses to all of the epitopes corresponding to the peptides used. This vaccine may be used in the treatment of various cancers. The cancers can also be selected from lung cancer such as NSCLC (non-small cell lung cancer) and small cell lung cancer, melanoma, mesothelioma, breast cancers, primary brain cancers, brain metastasis cancers, ovarian, uterine carcinoma, especially uterine corpus and/or uterine cervix carcinoma, head and neck, colon, colorectal, gastro-intestinal, renal cancers, sarcoma, germ cell tumors, leukemia, lymphoma, testicular cancers, pancreatic cancers and bladder cancers. Especially, the cancer can be cancer colon and non-small cell lung carcinoma (NSCLC), especially in people who are at stage IIIB or IV and/or who express the HLA-A2 receptor. Alternatively, cancers can also be selected from pancreatic cancers, bladder cancers or cancers that expressed the tumor antigens targeted by the peptides, especially CEA, p53, HER-2/neu, MAGE-2 and MAGE-3. Patients responding to a treatment with the emulsion prepared according to this invention may be identified by the HLA-2 biomarker measured in blood samples by different methods such as RT-PCR.

The ready to use product can be used for treating cancers alone or in combination with another therapy, in particular chemotherapies, targeted therapies or other immunotherapies such as checkpoint inhibitors.

For instance, the chemotherapy can be selected among cisplatin, carboplatin, cyclophosphamide, etoposide, teniposide, mitomycin, irinotecan, vinorelbine, etoposide, ifosfamide, temozolomide, fluorouracil (5FU), docetaxel, pemetrexed, navelbine, drugs that target tumor blood vessel growth (VEGF) such as bevacizumab, ramucirumab; prednisone; tyrosine kinase inhibitors targeting EGFR such as gefitinib, erlotinib, afatinib; ALK inhibitors such as crizotinib; ceritinib and any combination thereof.

In a preferred embodiment, the ready-to-use vaccine of the present invention is used in combination with a checkpoint inhibitor, especially a CTLA-4 inhibitor and/or a PD-1 or PD-L1 inhibitor; IDO inhibitors. The treatment with the checkpoint inhibitor can be performed before, simultaneously or after the treatment with the ready-to-use vaccine as disclosed herein.

The present invention relates to a kit or product comprising (a) the therapeutic effective amount of ready-to-use vaccine as disclosed herein; and (b) a check point inhibitor, preferably a CTLA-4 inhibitor and/or PD-1 or PD-L1 inhibitor, as a combined preparation for simultaneous, separate or sequential use, in particular in the treatment of cancer.

In a preferred embodiment, the treatment with a checkpoint inhibitor is performed after the treatment with the ready-to-use vaccine as disclosed herein.

Several PD-1/PD-L1 inhibitors are already available or under clinical development. For instance, the PD-1/PD-L1 inhibitors can be chosen among the non-exhaustive list including pembrolizumab (Merk), nivolumab (Bristol Myers Squibb), pidilizumab (Cure Tech), BMS936559 (Bristol Myers Squibb), MEDI4736 (Astra Zeneca), AMP-224 (Astra Zeneca), AMP-514 (Astra Zeneca), MPDL328OA (Roche), avelumab (also known as MSB0010718C from Merck KgA Serono/Pfizer). For instance, the PD-1/PD-L1 inhibitors can be chosen among those disclosed in WO2013/079174.

Extemporaneous Emulsion

The present invention also relates to a process for preparing an emulsion for parenteral administration, comprising the preparation of a suspension according to the present invention, followed by mixing said suspension with a water-in-oil emulsifier.

The present invention further relates to a kit comprising a sterile container comprising a suspension prepared by the method according to the present invention, a container, such as a vial, comprising a water-in-oil emulsifier and optionally a connector. Examples of suitable emulsifiers are as disclosed above and are preferably selected from mannide mono-oleate, sorbitan mono-oleate and adjuvants consisting of mixtures of 5-20% of mannide mono-oleate or sorbitan mono-oleate with 80-95% mineral oil (incomplete Freund's adjuvant, Montanide® ISA 51 and NH2 emulsion) or squalene (Montanide® ISA 720). In a preferred embodiment, the emulsifier comprises mannide mono-oleate (such as Montanide® ISA 51).

The kit may further comprise a connector.

The suspension obtained as described above may then be mixed with a water-in-oil emulsifier so as to obtain a water-in-oil emulsion, which is deemed to help presentation of the peptides to the dendritic cells. In this kind of emulsion, the water phase containing the peptides is entrapped in the form of droplets into the oil continuous phase, which allows for slower release of antigens from a depot and therefore stronger long-term immunity as compared to oil-in-water emulsions. Examples of such emulsifiers are mannide mono-oleate, sorbitan mono-oleate and adjuvants consisting of mixtures of 5-20% of mannide mono-oleate or sorbitan mono-oleate with 80-95% mineral oil (incomplete Freund's adjuvant, Montanide® ISA 51 and NH2 emulsion) or squalene (Montanide® ISA 720). According to a preferred embodiment of this invention, the emulsifier is a mixture of mannide mono-oleate (8-12%) with mineral oil (88-92%) which may be obtained from SEPPIC under the trade name Montanide® ISA 51. It is assumed that mineral oil is only partly metabolized, rendering it more efficient at inducing an immune response than non-mineral oil-based adjuvants, particularly in the case of weak immunogens. Usually, to obtain the emulsion, one volume of any of the above emulsifiers is mixed with one volume of the peptide suspension, under aseptic conditions.

The resulting emulsion may be a "bedside" formulation which is prepared extemporaneously, just prior to treatment of the patient. More specifically, the emulsion can be prepared extemporaneously using a connector linked to a syringe containing the emulsion and another syringe containing the emulsifier, according to the process checked: 20 slow cycles (9 s per cycle—180 s) followed by 40 fast cycles (20 s). The emulsifier and the suspension are preferably stored at a temperature below room temperature and brought to room temperature immediately before mixing. The resulting emulsion may be injected to the patient within 8 hours from the preparation of the emulsion and preferably within 4 hours. The emulsion may be administered parenterally and used as a vaccine to elicit T-lymphocyte responses to all of the epitopes corresponding to the peptides used. This vaccine may be used in the treatment of various cancers, especially cancer colon and non-small cell lung carcinoma (NSCLC), especially in people who are at stage IIIB or IV and/or who express the HLA-A2 receptor. The cancers can also be selected from pancreatic cancers, bladder cancers or cancers that expressed the tumor antigens targeted by the peptides, especially CEA, p53, HER-2/neu, MAGE-2 and MAGE-3. The ready to use product can be used for treating cancers alone or in combination with another therapy, in particular chemotherapies, targeted therapies or other immunotherapies such as checkpoint inhibitors, in particular as disclosed above.

This invention will be better understood in light of the following examples which are given for illustrative purposes only and do not intend to limit the scope of the invention, which is defined by the attached claims.

EXAMPLES

Example 1: Preparation of a Suspension According to the Invention

Ten peptides were synthesized by PolyPeptide (San Diego, Calif.) using standard Boc or Fmoc solid phase chemistry:

```
                                          (SEQ ID NO: 1)
             aKXVAAWTLKAAa = MPS-7, (SEQ ID NO: 5)
             SMPPPGTRV = MPS-103, (SEQ ID NO: 9)
             IMIGHLVGV = MPS-214, (SEQ ID NO: 10)
             KVAEIVHFL = MPS-215, (SEQ ID NO: 8)
             YLSGADLNL = MPS-200, (SEQ ID NO: 6)
             KLBPVQLWV = MPS-102, (SEQ ID NO: 4)
             LLTFWNPPV = MPS-213, (SEQ ID NO: 2)
             RLLQETELV = MPS-112, (SEQ ID NO: 3)
             YLQLVFGIEV = MPS-106,
             and (SEQ ID NO: 7)
             KVFGSLAFV = MPS-216.
```

These peptides were purified by HPLC and their identities were verified by mass spectrometry.

Three solutions were prepared are described in Table 1.

TABLE 1

| Solution | Dilution solvent | Peptides | Concentration of each peptide in solution |
|---|---|---|---|
| Solution 1 | Acetic acid 0.1875M | MPS-7 MPS-103 MPS-214 MPS-215 | 3.4 mg/ml |

TABLE 1-continued

| Solution | Dilution solvent | Peptides | Concentration of each peptide in solution |
|---|---|---|---|
| Solution 2 | Sodium hydroxide 0.05M | MPS-102 MPS-106 MPS-112 MPS-200 MPS-213 | 2.72 mg/ml |
| Solution 3 | DMSO | MPS-216 | 10.9 mg/ml |

Solutions 1 and 2 were prepared at room temperature using vortex agitation and/or sonication for a few minutes, while solution 3 was prepared under heating at 37° C. using vortex agitation. These solutions were then stored at 2-8° C. for up to four hours in order to assess their degradation during potential holding times in their industrial manufacturing process. Their degradation was assessed by liquid chromatography coupled with UV detection and mass spectrometry. The results of the analysis performed are summarized in Table 2.

TABLE 2

| Solution | Dilution solvent | 4 hours at Room Temperature | 4 hours at 2-8° C. |
|---|---|---|---|
| Solution 1 | Acetic acid 0.1875M | No degradation | No degradation |
| Solution 2 | Sodium hydroxide 0.05M (pH = 12.7) | Not tested | No significant degradation |
| Solution 3 | DMSO | No degradation | No degradation |

The above solutions were thus stored for less than 4 hours at 2-8° C., then sterile filtered and blended together in a A:B:C mass ratio of 2.9:3.6:1, to obtain a suspension, the pH of which was adjusted to 7 by adding thereto 0.2 ml of a 62.5 mM sodium phosphate solution and a 0.5 M NaOH solution.

The suspension was stored at −20° C. in a sterile vial.

Example 2: Comparative Experiment

Peptide solutions were prepared, which were identical to Solution 2 described in Example 1, except that the amount of sodium hydroxide was varied from 0.10 M (as described in WO 2004/094454) to 0.013 M.

The ability of these media to solubilize the peptides while preventing their degradation after two hours storage at 2-8° C. was assessed. The results are summarized in Table 3.

TABLE 3

| Solution 2 | pH | Solubilisation | 2 hours at 2-8° C. |
|---|---|---|---|
| 0.10M | 13 | Complete | Significant degradation of MPS-200 |
| 0.05M | 12.7 | Complete | No degradation |
| 0.025M | 12.4 | Incomplete | Not performed |
| 0.013M | 12 | Incomplete | Not performed |

From this table, it can be derived that a pH at or below 12.4 does not allow for the proper solubilizing of the peptides, whereas a pH at or above 13 results in the degradation of one of the peptides. Mass Spectroscopy analysis was performed in order to identify the degradation products that were formed. It was found that the Asn or Gln's side chains were hydrolyzed to Asp and Glu, respectively.

This experiment demonstrates that the pH of solution 2 should be adjusted to 12.5-12.9.

Example 3: Stability of the Suspension

An additional test was set up to assess possible peptide aggregation as described below. This method is able to monitor peptide aggregation and is sensitive, specific and accurate. It was suitable for monitoring structural and mass modifications or variants that may occur during manufacturing or during storage. A Liquid Chromatography-Mass Spectroscopy (LC-UV/MS) was carried out to be sure of the identity of the peptides and the absence of covalent bonds between them. The method was developed to check the absence of aggregation between peptides despite the presence of precipitates of some peptides. The aim was to determine if any covalent bonds could be established between the peptides contained in the suspension of Example 1 during 9 months of storage at different conditions: −20° C.; +5° C. and +25° C.

Each peptide was identified by its retention time in UV spectrum and by mass.

Chromatographic Conditions
    Column: Advance Bio Peptide Mapping LC column, 2.1*250 mm, 2.7 µm, C18, 120 Å,
    Agilent reference no 651750-902
    Detection: 215 nm and 280 nm
    Flow rate: 0.3 ml/min
    Injection volume: 5 µl
    Run time: 100 min
    Column temperature: 35° C.±2° C.
    Sample temperature: 5° C.
    Needle wash: 0.1% Trifluoroacetic acid (TFA) in dimethylsulfoxide (DMSO)
    Mobile phase: Eluent A: 0.2% TFA in 5% acetonitrile
    Eluent B: 0.2% TFA in 95% acetonitrile
    Gradient table:

| Time (min) | Flow rate | % Eluent B | Pressure limit (Bar) |
|---|---|---|---|
| 0 | 0.3 | 0 | 600 |
| 50 | 0.3 | 50 | 600 |
| 81 | 0.3 | 100 | 600 |
| 85 | 0.3 | 100 | 600 |
| 86 | 0.3 | 0 | 600 |
| 120 | 0.3 | 0 | 600 |

Preparation of Sample Solution

Transfer the content of 1 vial (~1 ml) containing the suspension of Example 1 in a 10 ml volumetric flask and complete to volume with 0.1% TFA in DMSO. The vial is weighed before and after sampling in order to determine the exact sample weight.

The suspension of Example 1 was analyzed by the Liquid Chromatography/Mass Spectroscopy (LC/MS) method.

The results obtained show that at all storage conditions, all the peptides are detected. There are no significant differences between the chromatograms, whatever the storage conditions. The relative UV-peak areas did not change. Full MS scan did not detect additional masses, including potential masses at high molecular weight that would correspond to covalent aggregates. This means that no covalent bonds were established between the peptides during these 3 months of storage.

The result of this analysis is that no covalent bonds between peptides were observed in the suspension, which would subsequently lead to chemical aggregation.

After three months at three storage conditions (−20° C., +5° C. and +25° C.), the observed retention times and molecular weight (MW) strictly correspond to the active-ingredient peptides and remains within the specification level determined at batch release. The results demonstrate the absence of aggregation and that covalent bonds between peptides do not occur in the suspension during manufacturing and storage.

Example 4: Preparation of an Extemporaneous W/O Emulsion According to the Invention In order to prepare an injectable clinical product, a water-in-oil emulsion was formed by mixing the suspension of Example 1 with a water-in-oil emulsifying mixture (Montanide® ISA 51 supplied by SEPPIC, stored in the dark at 2-8° C. in a vial) in a 1:1 mass ratio, corresponding to 0.9 ml of peptide suspension and 1.1 ml of emulsifier. Specifically, the suspension and the emulsifier were brought to room temperature immediately before mixing and transferred each in a syringe. The emulsion was prepared extemporaneously by means of a plastic connector linked to these syringes. The plunger of the syringes were alternately pushed slowly 20 times each, then 40 times each at a high speed. From any of the syringes, 1 ml of this emulsion may be injected to the patient by subcutaneous way.

Example 5: Preparation of a Ready-to-Use W/O Emulsion According to the Invention In order to prepare an injectable clinical delivery product, a water-in-oil emulsion was formed by mixing the suspension of Example 1 with an oily adjuvant (Montanide® ISA 51 supplied by SEPPIC) in a 1:1 mass ratio. To prepare the emulsion, the mixer bag of the device was first inflated with nitrogen so as to provide an inert gas blanket in operation. 5200 g of the emulsifier was filtered, then transferred under aseptic conditions to the mixing chamber of an Allegro® mixer comprising an axial flow turbine. The rotation speed of the impeller was set to 200 rpm, then 5200 g of the suspension described above were slowly (within 1-2 min) added to the mixing chamber, under aseptic conditions. Stirring was continued for 5 minutes.

A white emulsion free from visible particles was obtained, which had a viscosity of 280 mPa·s and could be easily transferred through a 26 Ga needle out of a 1 mL syringe.

Example 6: Preparation of Emulsions Using Different Stirring Times

Emulsions according to this invention were prepared as described in Example 5, using different stirring times. The initial concentrations of the various peptides are reported in the tables below.

| 5 minutes | Concentration |
|---|---|
| MPS-103 | 0.53 |
| MPS-200 | 0.57 |
| MPS-112 | 0.56 |
| MPS-214 | 0.53 |
| MPS-7 | 0.58 |
| MPS-215 | 0.58 |
| MPS-216 | 0.55 |
| MPS-102 | 0.56 |
| MPS-213 | 0.56 |
| MPS-106 | 0.54 |

| 10 minutes | Concentration (mg/ml) |
|---|---|
| MPS-103 | 0.56 |
| MPS-200 | 0.57 |
| MPS-112 | 0.57 |
| MPS-214 | 0.53 |
| MPS-7 | 0.58 |
| MPS-215 | 0.58 |
| MPS-216 | 0.56 |
| MPS-102 | 0.57 |
| MPS-213 | 0.56 |
| MPS-106 | 0.54 |

| 15 minutes | Concentration |
|---|---|
| MPS-103 | 0.54 |
| MPS-200 | 0.57 |
| MPS-112 | 0.56 |
| MPS-214 | 0.53 |
| MPS-7 | 0.57 |
| MPS-215 | 0.58 |
| MPS-216 | 0.55 |
| MPS-102 | 0.56 |
| MPS-213 | 0.56 |
| MPS-106 | 0.53 |

From the above tables, it can be derived that the concentration of the various peptides remain within the 0.49-0.59 mg/ml range, whatever the stirring time. The emulsion can thus be prepared using a short stirring time of 5 minutes only.

Example 7: Chemical Stability of the Emulsion

The chemical stability of the peptides contained in the emulsion prepared according to Example 5 is assessed by means of the following method.

A sample of 0.9 g of the emulsion of Example 5 is accurately weighted and mixed with 0.1% TFA in DMSO so as to fill a 5 mL volumetric flask. The mixture is then vortexed for 2 minutes and centrifuged for 7 minutes at 4000 rpm. The lower layer is then analyzed by Liquid Chromatography/Mass Spectroscopy (LC/MS) using the following chromatographic conditions:

Column: Advance Bio Peptide Mapping LC column, 2.1×250 mm, 2.7 µm, C18, 120 Å,

Agilent® reference n°651750-902 or equivalent

Detection: 215 nm and 280 nm

Flow rate: 0.3 ml/min

Injection volume: 5 µl

Run time: 100 min

Column temperature: 35° C.±2° C.

Sample temperature: 5° C.

Needle wash: 0.1% Trifluoroacetic acid (TFA) in dimethylsulfoxide (DMSO)

Mobile phase: Eluent A: 0.2% TFA in 5% acetonitrile

Eluent B: 0.2% TFA in 95% acetonitrile

Gradient table:

| Time (min) | Flow rate | % Eluent B | Pressure limit (Bar) |
|---|---|---|---|
| 0 | 0.3 | 0 | 600 |
| 50 | 0.3 | 50 | 600 |
| 81 | 0.3 | 100 | 600 |
| 85 | 0.3 | 100 | 600 |
| 86 | 0.3 | 0 | 600 |
| 100 | 0.3 | 0 | 600 |

A standard solution is prepared by transferring 0.9 mL of the batch suspension described in Example 1 with 1.1 mL of Montanide ISA 51 in a 10.0 mL volumetric flask, then vortexing and centrifuging the mixture as described above. The lower layer thus obtained is analyzed in the same conditions as above.

The concentration of each peptide is expressed in mg/g using the formula:

$$\text{Concentration (mg/g)} = \frac{A}{S} \times \frac{0.9X}{10} \times 5 \times \frac{1}{W}$$

where:
A: is the peak area of each peptide in the sample solution
S: is the peak area of each peptide in the standard solution
W: is the sample weight expressed in g The results obtained on samples of the emulsion of Example 5 stored under different conditions show that at all storage conditions, all the peptides are detected with no significant differences between the chromatograms, which means that no covalent bonds between peptides are observed in the emulsion. Moreover, the relative UV-peak areas do not change. Full MS scan does not detect additional masses, including potential masses at high molecular weight. This means that no covalent bonds or aggregates are established between the peptides under these different storage conditions.

Especially, after one month under three storage conditions (−20° C., +5° C. and +25° C.), the observed retention times and molecular weight (MW) correspond to the active-ingredient peptides and remain within the specification level determined at batch release, that is ±10%, as shown below:

| Peptide | Initial content (mg/g) | Content after 2 month at −20° C. (mg/g) | Content after 2 month at 5° C. (mg/g) | Content after 2 month at 25° C. (mg/g) |
|---|---|---|---|---|
| MPS-103 | 0.55 | 0.55 | 0.54 | 0.54 |
| MPS-200 | 0.58 | 0.56 | 0.56 | 0.55 |
| MPS-112 | 0.57 | 0.55 | 0.55 | 0.55 |
| MPS-214 | 0.53 | 0.51 | 0.51 | 0.50 |
| MPS-7 | 0.58 | 0.56 | 0.56 | 0.56 |
| MPS-215 | 0.58 | 0.57 | 0.56 | 0.56 |
| MPS-216 | 0.56 | 0.54 | 0.54 | 0.53 |
| MPS-102 | 0.57 | 0.55 | 0.55 | 0.55 |
| MPS-213 | 0.56 | 0.55 | 0.54 | 0.54 |
| MPS-106 | 0.56 | 0.56 | 0.55 | 0.54 |

Example 8: Physical Stability of the Emulsion

The droplet sizes of various samples of the emulsion prepared as described in Example 5 were determined by laser diffraction using a granulometer (Malvern mastersizer 3000E optical system). These samples were collected from different areas of the mixer. The results were expressed as the maximum size of x % of the droplets, i.e. Dx. They are summarized in the table below.

| Sample collected | D10 (µm) | D50 (µm) | D90 (µm) |
|---|---|---|---|
| Bottom of mixer | 1.05 | 10.5 | 19.4 |
| Middle of mixer | 0.87 | 8.8 | 17.5 |
| Top of mixer | 1.04 | 10.3 | 19.1 |

This experiment shows that the droplet sizes are homogeneous throughout the mixer, with a D50 of about 10 µm.

The variation in the droplet sizes was measured after one month storage under different conditions. As shown in the table below, the droplet size remained substantially constant:

| | Initial droplet size (µm) | Droplet size after 1 month at −20° C. (µm) | Droplet size after 1 month at −20° C. (µm) | Droplet size after 1 month at −20° C. (µm) |
|---|---|---|---|---|
| $D_{10}$ | 0.99 | 0.77 | 0.84 | 1.66 |
| $D_{50}$ | 9.67 | 9.55 | 9.21 | 11.10 |
| $D_{90}$ | 18.70 | 19.10 | 18.30 | 20.20 |
| $D_{4.3}$ | 10.10 | 9.85 | 9.70 | 11.30 |

Example 9: Immunogenicity

Some peptides were identified as partly or totally precipitated in the suspension prepared as described in Example 1:

```
MPS-216
                              (SEQ ID NO: 7)
KVFGSLAFV (33% of solubility)

MPS-215
KVAEIVHFL (56% of solubility)

MPS-106
YLQLVFGIEV (0% of solubility)
```

The immunogenicity of each peptide entering in the combination even in poorly soluble or insoluble state was tested in vivo in HLA A2.1/k transgenic mice.

CTL (Cytotoxic T lymphocyte) and HLT (Helper T lymphocyte) induction by the Elispot assay was performed to measure IFN gamma production, the spots were counted by computer assisted analysis production.

The net spots/$10^6$ CD8+ cells (CTL) or CD4+ cells (HTL) were calculated as (number of spots against relevant peptide)−(number of spots with irrelevant peptide)×2.5.

The data accumulated from 6 independent experiments demonstrated that the combination was immunogenic with induction of CTL responses.

The range observed was 50 to 200 Standard Units against a very soluble peptide such as MPS 214.

Unexpectedly the same range (50 to 200 SU) of response was observed with the 3 poorly soluble peptides [MPS-215 (KVAEIVHFL) with 56% of solubility; MPS-216 (KVFGSLAFV (SEQ ID NO:7)) with 33% of solubility; MPS-106 (YLQLVFGIEV) 0% of solubility].

Soluble, insoluble or poorly soluble epitopes in the new emulsion were capable to induce strong CTL responses. The solubility state of poorly soluble peptides in the final emulsion does not affect the in vivo immunogenic properties in HLA A2 Transgenic model.

Example 10: Comparative Experiment

The suspension prepared as described in Example 1 was mixed with the same adjuvant, in the same ratio, except that mixing was conducted by means of a high shear mixer (Silverson® Verso) having a rotor-stator configuration. Stirring rates of 2000 and 8000 rpm were used for 15 min and 2 min, respectively: a very thick cream was obtained which could not be used as an injectable product. Other batches obtained with the same mixer at 5000 and 8000 rpm led to peptide degradation. Specifically, 8.5% oxidation of peptide SMPPPGTRV (SEQ ID NO: 5) was noted after 6 weeks storage at 4° C. and still 2% oxidation at −20° C. Moreover, 16.5% oxidation was noted for peptide IMIGHLVGV (SEQ ID NO:9) after 6 weeks storage at 4° C. and still 4% oxidation at −20° C.

This experiment demonstrates that a high shear mixer does not allow the preparation of an injectable emulsion for the stable delivery of peptides.

The invention claimed is:

1. A method for manufacturing a ready-to-use peptide emulsion on the industrial scale, comprising the step of emulsifying a suspension of at least two peptides under low shear conditions, at a rotation speed of between 100 and 1000 rpm, for 2 to 20 minutes, with at least one adjuvant.

2. The method according to claim 1, characterized in that the peptides comprise at least one soluble peptide and at least one non-soluble peptide.

3. The method according to claim 2, characterized in that the peptides are selected from the group consisting of: a peptide KVFGSLAFV (SEQ ID NO:7), a peptide YLSGADLNL (SEQ ID NO:8), a peptide KLBPVQLWV with B indicating α-aminoisobutyric acid (SEQ ID NO:6), a peptide SMPPPGTRV (SEQ ID NO:5), a peptide IMIGHLVGV (SEQ ID NO:9), a peptide LLTFWNPPV (SEQ ID NO:4), a peptide RLLQETELV (SEQ ID NO:2), a peptide aKXVAAWTLKAAa with X and a respectively indicating cyclohexylalanine and d-alanine (SEQ ID NO:1), a peptide YLQLVFGIEV (SEQ ID NO:3) and a peptide KVAEIVHFL (SEQ ID NO:10).

4. The method according to claim 3, characterized in that the suspension comprises a combination of a peptide KVFGSLAFV (SEQ ID NO:7), a peptide YLSGADLNL (SEQ ID NO:8), a peptide KLBPVQLWV (SEQ ID NO:6), a peptide SMPPPGTRV (SEQ ID NO:5), a peptide IMIGHLVGV (SEQ ID NO:9), a peptide LLTFWNPPV (SEQ ID NO:4), a peptide RLLQETELV (SEQ ID NO:2), a peptide aKXVAAWTLKAAa with X and a respectively indicating cyclohexylalanine and d-alanine (SEQ ID NO:1), a peptide YLQLVFGIEV (SEQ ID NO:3) and a peptide KVAEIVHFL (SEQ ID NO:10).

5. The method according to claim 1, characterized in that the adjuvant consists of a mixture of a hydrocarbon oil with a water-in-oil emulsifier.

6. The method according to claim 5, characterized in that the hydrocarbon oil is selected from paraffin oil, a vegetable oil, squalene, squalane or a mineral oil and the water-in-oil emulsifier is selected from mannide mono-oleate and sorbitan mono-oleate.

7. The method according to claim 5, characterized in that the weight ratio of the adjuvant to the peptide suspension ranges from: 10:1 to 1:10; 5:1 to 1:5, 2:1 to 1:2, or 1:1.

8. The method according to claim 1, characterized in that all or part of the mixing step is performed under an inert atmosphere.

9. The method according to claim 1, characterized in that the volume of the emulsion is greater than 5 L.

10. The method according to claim 3, characterized in that the peptide suspension is prepared by a method comprising:
   a) preparing at least three different solutions A, B and C, wherein:
      solution A being an acidic aqueous medium and comprising a peptide aKXVAAWTLKAAa (SEQ ID NO:1) with X and a respectively indicating cyclohexylalanine and d-alanine (SEQ ID NO:1),
      solution B being a basic aqueous medium with a pH of between 12.5 and 12.9 before adding any peptide thereto and solution B comprising a peptide YLSGADLNL (SEQ ID NO:8),
      solution C being DMSO and comprising a peptide KVFGSLAFV (SEQ ID NO:7), and
      solutions A and/or B further comprise at least three additional peptides selected from: KLBPVQLWV with B indicating α-aminoisobutyric acid (SEQ ID NO:6), SMPPPGTRV (SEQ ID NO:5), IMIGHLVGV (SEQ ID NO:9), LLTFWNPPV (SEQ ID NO:4), KVAEIVHFL (SEQ ID NO:10), RLLQETELV (SEQ ID NO:2) and YLQLVFGIEV (SEQ ID NO:3);
   b) mixing said solutions so as to form a suspension, and
   c) adjusting the pH of said suspension to about 7.

11. The method according to claim 10, wherein the solution A comprises aKXVAAWTLKAAa (SEQ ID NO:1), SMPPPGTRV (SEQ ID NO:5), IMIGHLVGV (SEQ ID NO:9) and KVAEIVHFL (SEQ ID NO:10) and the solution B comprises YLSGADLNL (SEQ ID NO:8), KLBPVQLWV (SEQ ID NO:6), LLTFWNPPV (SEQ ID NO:4), RLLQETELV (SEQ ID NO:2) and YLQLVFGIEV (SEQ ID NO:3).

* * * * *

UNITED STATES PATENT AND TRADEMARK OFFICE
CERTIFICATE OF CORRECTION

PATENT NO. : 11,325,959 B2
APPLICATION NO. : 16/477534
DATED : May 10, 2022
INVENTOR(S) : Jean-Pascal Conduzorgues Page 1 of 1

It is certified that error appears in the above-identified patent and that said Letters Patent is hereby corrected as shown below:

On the Title Page

(74) Attorney, Agent, or Firm, "Saliwanchik, Lloyd & Eisenchenk" should read --Saliwanchik, Lloyd & Eisenschenk--.

In the Specification

Column 4,
Line 57, "aKXVAAWTLKAAa with X and a" should read --$a$KXVAAWTLKAAa with X and $a$--.
Line 67, "aKXVAAWTLKAAa with X and a" should read --$a$KXVAAWTLKAAa with X and $a$--.

Column 6,
Lines 63-64, "aKXVAAWTLKAAa with X and a" should read --$a$KXVAAWTLKAAa with X and $a$--.

Column 13,
Lines 11-12,
"those disclosed in WO2013/079174.
Extemporaneous Emulsion" should read
--those disclosed in WO2013/079174.
    For instance, the CTLA-4 inhibitors can be chosen among the non-exhaustive list including Tremelimumab (Pfizer Medimmune ) and ipilimumab (BMS).
Extemporaneous Emulsion--.

In the Claims

Column 29,
Line 29, "aKXVAAWTLKAAa with X and a" should read --$a$KXVAAWTLKAAa with X and $a$--.
Line 40, "aKXVAAWTLKAAa with X and a" should read --$a$KXVAAWTLKAAa with X and $a$--.

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 22

<210> SEQ ID NO 1
<211> LENGTH: 13
<212> TYPE: PRT
<213> ORGANISM: artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is d-alanine
<220> FEATURE:
<221> NAME/KEY: MISC_FEATURE
<222> LOCATION: (3)..(3)
<223> OTHER INFORMATION: Xaa is a cyclohexylalanine
<220> FEATURE:
<221> NAME/KEY: MISC_FEATURE
<222> LOCATION: (13)..(13)
<223> OTHER INFORMATION: Xaa is d-alanine

<400> SEQUENCE: 1

Xaa Lys Xaa Val Ala Ala Trp Thr Leu Lys Ala Ala Xaa
1               5                   10

<210> SEQ ID NO 2
<211> LENGTH: 9
<212> TYPE: PRT
<213> ORGANISM: artificial sequence
<220> FEATURE:
<223> OTHER INFORMATION: peptide

<400> SEQUENCE: 2

Arg Leu Leu Gln Glu Thr Glu Leu Val
1               5

<210> SEQ ID NO 3
<211> LENGTH: 10
<212> TYPE: PRT
<213> ORGANISM: artificial sequence
<220> FEATURE:
<223> OTHER INFORMATION: peptide

<400> SEQUENCE: 3

Tyr Leu Gln Leu Val Phe Gly Ile Glu Val
1               5                   10

<210> SEQ ID NO 4
<211> LENGTH: 9
<212> TYPE: PRT
<213> ORGANISM: artificial sequence
<220> FEATURE:
<223> OTHER INFORMATION: peptide

<400> SEQUENCE: 4

Leu Leu Thr Phe Trp Asn Pro Pro Val
1               5
```

```
<210> SEQ ID NO 5
<211> LENGTH: 9
<212> TYPE: PRT
<213> ORGANISM: artificial sequence
<220> FEATURE:
<223> OTHER INFORMATION: peptide

<400> SEQUENCE: 5

Ser Met Pro Pro Pro Gly Thr Arg Val
1               5

<210> SEQ ID NO 6
<211> LENGTH: 9
<212> TYPE: PRT
<213> ORGANISM: artificial sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: xaa is alpha-aminobutyric acid

<400> SEQUENCE: 6

Lys Leu Xaa Pro Val Gln Leu Trp Val
1               5

<210> SEQ ID NO 7
<211> LENGTH: 9
<212> TYPE: PRT
<213> ORGANISM: artificial sequence
<220> FEATURE:
<223> OTHER INFORMATION: peptide

<400> SEQUENCE: 7

Lys Val Phe Gly Ser Leu Ala Phe Val
1               5

<210> SEQ ID NO 8
<211> LENGTH: 9
<212> TYPE: PRT
<213> ORGANISM: artificial sequence
<220> FEATURE:
<223> OTHER INFORMATION: peptide

<400> SEQUENCE: 8

Tyr Leu Ser Gly Ala Asp Leu Asn Leu
1               5

<210> SEQ ID NO 9
<211> LENGTH: 9
<212> TYPE: PRT
<213> ORGANISM: artificial sequence
<220> FEATURE:
<223> OTHER INFORMATION: peptide

<400> SEQUENCE: 9

Ile Met Ile Gly His Leu Val Gly Val
1               5

<210> SEQ ID NO 10
<211> LENGTH: 9
<212> TYPE: PRT
<213> ORGANISM: artificial sequence
<220> FEATURE:
<223> OTHER INFORMATION: peptide

<400> SEQUENCE: 10
```

```
Lys Val Ala Glu Ile Val His Phe Leu
1               5

<210> SEQ ID NO 11
<211> LENGTH: 9
<212> TYPE: PRT
<213> ORGANISM: artificial
<220> FEATURE:
<223> OTHER INFORMATION: peptide

<400> SEQUENCE: 11

Phe Leu Asp Glu Phe Met Glu Gly Val
1               5

<210> SEQ ID NO 12
<211> LENGTH: 9
<212> TYPE: PRT
<213> ORGANISM: artificial sequence
<220> FEATURE:
<223> OTHER INFORMATION: peptide

<400> SEQUENCE: 12

Val Val Met Ser Trp Ala Pro Pro Val
1               5

<210> SEQ ID NO 13
<211> LENGTH: 10
<212> TYPE: PRT
<213> ORGANISM: artificial sequence
<220> FEATURE:
<223> OTHER INFORMATION: peptide

<400> SEQUENCE: 13

Leu Leu Leu Asp Asp Leu Leu Val Ser Ile
1               5                   10

<210> SEQ ID NO 14
<211> LENGTH: 10
<212> TYPE: PRT
<213> ORGANISM: artificial sequence
<220> FEATURE:
<223> OTHER INFORMATION: peptide

<400> SEQUENCE: 14

Ser Leu Ala Asp Glu Ala Glu Val Tyr Leu
1               5                   10

<210> SEQ ID NO 15
<211> LENGTH: 9
<212> TYPE: PRT
<213> ORGANISM: artificial sequence
<220> FEATURE:
<223> OTHER INFORMATION: peptide

<400> SEQUENCE: 15

Val Leu His Asp Asp Leu Leu Glu Ala
1               5

<210> SEQ ID NO 16
<211> LENGTH: 10
<212> TYPE: PRT
<213> ORGANISM: artificial sequence
<220> FEATURE:
<223> OTHER INFORMATION: peptide

<400> SEQUENCE: 16

Gly Ile Val Glu Gly Leu Ile Thr Thr Val
```

```
<210> SEQ ID NO 17
<211> LENGTH: 10
<212> TYPE: PRT
<213> ORGANISM: artificial sequence
<220> FEATURE:
<223> OTHER INFORMATION: peptide

<400> SEQUENCE: 17

Ser Leu Phe Glu Gly Ile Asp Ile Tyr Thr
1               5                   10

<210> SEQ ID NO 18
<211> LENGTH: 10
<212> TYPE: PRT
<213> ORGANISM: artificial sequence
<220> FEATURE:
<223> OTHER INFORMATION: peptide

<400> SEQUENCE: 18

Phe Ile Ala Ser Asn Gly Val Lys Leu Val
1               5                   10

<210> SEQ ID NO 19
<211> LENGTH: 9
<212> TYPE: PRT
<213> ORGANISM: artificial sequence
<220> FEATURE:
<223> OTHER INFORMATION: peptide

<400> SEQUENCE: 19

Ile Leu Asn Ala Met Ile Ala Lys Ile
1               5

<210> SEQ ID NO 20
<211> LENGTH: 10
<212> TYPE: PRT
<213> ORGANISM: artificial sequence
<220> FEATURE:
<223> OTHER INFORMATION: peptide

<400> SEQUENCE: 20

Gly Leu Phe Gly Asp Ile Tyr Leu Ala Ile
1               5                   10

<210> SEQ ID NO 21
<211> LENGTH: 9
<212> TYPE: PRT
<213> ORGANISM: artificial sequence
<220> FEATURE:
<223> OTHER INFORMATION: peptide

<400> SEQUENCE: 21

Ile Leu Asp Lys Val Leu Val His Leu
1               5

<210> SEQ ID NO 22
<211> LENGTH: 10
<212> TYPE: PRT
<213> ORGANISM: artificial sequence
```

```
<220> FEATURE:
<223> OTHER INFORMATION: peptide

<400> SEQUENCE: 22

Ala Cys Asp Pro His Ser Gly His Phe Val
1               5                   10
```